United States Patent [19]

Dawson et al.

[11] Patent Number: 4,553,438

[45] Date of Patent: Nov. 19, 1985

[54] CENTRIFUGAL CARTON TESTER

[75] Inventors: Raymond L. Dawson, Monroe; Clayton Dodd, Farmerville; Bobby E. Harrell; Grady E. Lee, both of West Monroe, all of La.

[73] Assignee: Manville Service Corporation, Denver, Colo.

[21] Appl. No.: 601,893

[22] Filed: Apr. 19, 1984

[51] Int. Cl.[4] .............................................. G01N 3/08
[52] U.S. Cl. ................................................... 73/830
[58] Field of Search .......... 73/432 SD, 432 K, 432 R, 73/159, 826, 830, 838, 835

[56] References Cited

U.S. PATENT DOCUMENTS 3,290,929 12/1966 Sheldon ................................ 73/834

FOREIGN PATENT DOCUMENTS 207690 12/1923 United Kingdom ............ 73/432 K

Primary Examiner—Stewart J. Levy
Assistant Examiner—Robert R. Raevis
Attorney, Agent, or Firm—John D. Lister; Cornelius P. Quinn

[57] ABSTRACT

A centrifugal test apparatus for determining the failure point of a carton for packaging bottles or cans comprises a box mounted on a variable speed drive shaft which is adapted to receive at opposite ends a counterweight and a test carton. The test carton is attached to a force gauge by an attachment means that simulates the gripping of the test carton by a person.

5 Claims, 6 Drawing Figures

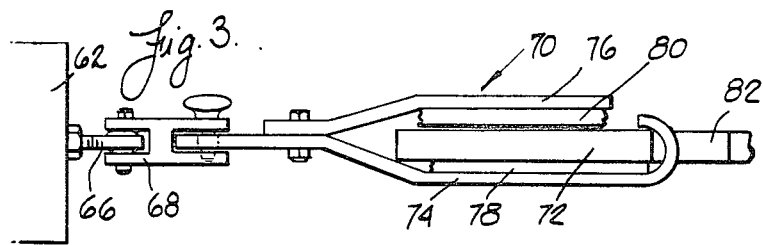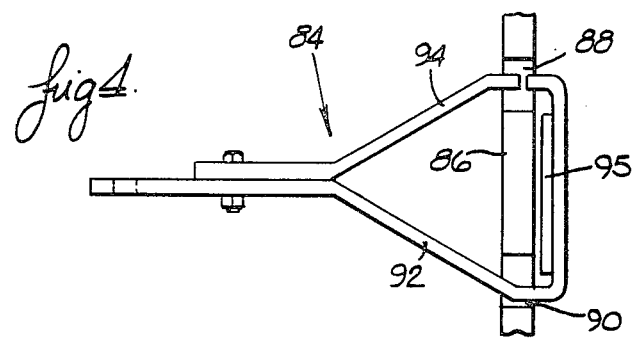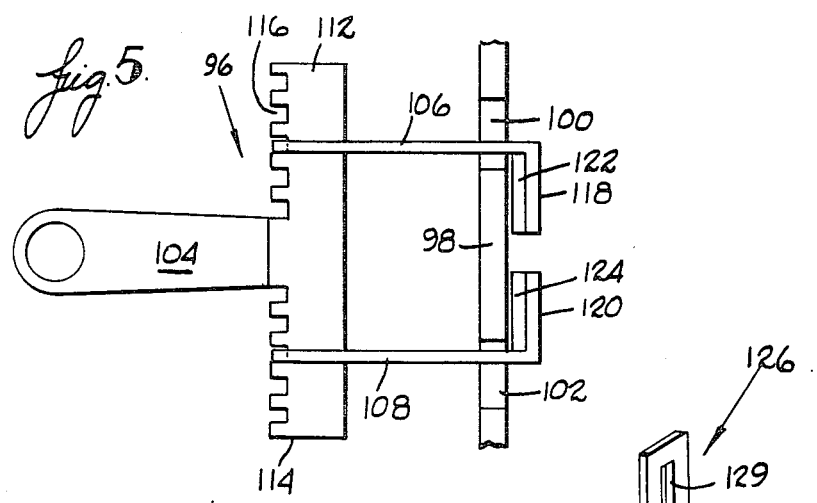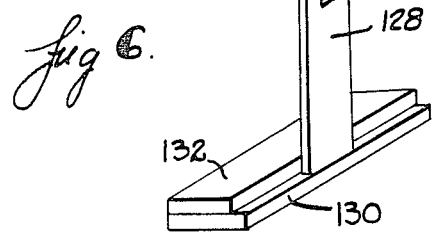

CENTRIFUGAL CARTON TESTER

BACKGROUND OF THE INVENTION

The present invention is directed to a carton tester and in particular to a centrifugal carton tester for testing carrier style paperboard cartons of the type used in the beverage industry.

Beverages such as soft drinks and beer are typically sold in bottles or cans which are packaged in carriers in lots of six, eight or twelve bottles or cans to a carrier. The collective weight of these bottles or cans in a carrier when combined with adverse conditions such as a wetting of the carrier and/or rough handling of the carrier can result in a failure of the carrier. Failure of a carrier in the handle region can result in the dropping of the entire carrier. Failure of other portions of a carrier can result in the release of one or more bottles or cans from the carrier. Accordingly, it is important to test such carriers to determine their failure points under various adverse conditions and to make sure the carriers are manufactured to certain standards.

The centrifugal force tester of the present invention has been developed to measure the force required to produce failure in a package designed to hold and support a relatively heavy product. It is primarily designed to test the carriers commonly used in the soft drink and beer beverage markets to carry multiple units of bottled or canned beverages.

It is contemplated that the centrifugal force carton tester can be used (1) to establish minimum standards for cartons (2) to monitor carton quality at the point of manufacture; and (3) to evaluate performance levels of cartons exposed to adverse environmental conditions such as refrigeration in storage or exposure to rain on open delivery trucks.

The weight of a package is that force exerted by gravity on the mass of the carton and its contents. Obviously for any package to be usable it must be able to support (or hold) a force equal to its own weight. In addition it must be able to withstand additional forces created during normal handling or abuse.

An example of an additional force is the force developed due to the angular acceleration of the package when a person walks and carries a carton with the normal swinging of the arms. The total maximum force so generated is limited to about twice the package weight.

Another force is the force generated when a package is taken from a height and lowered to a carrying position. The force on the carton at the end of this action again exceeds the package weight. This force is more difficult to predict but it is estimated to be up to two to three times the package weight.

The weight of a package is the force created by gravity on the mass of the carton and its contents. Mathematically, weight can be expressed by the following equation:

$$W = mg$$

where,
W = weight of package
m = mass of carton and its contents
g = acceleration of gravity = 32 ft/sec$^2$ This weight equation is a specific application of the general equation for force from physics:

$$F = ma$$

where,
F = force
m = mass
a = acceleration

In designing the tester of the present invention, it was decided to use the force created by angular acceleration when an object is rotated in a circular motion tethered to the axis of rotation. A force gauge is inserted in the tether between the axis of rotation and the carton being tested. The rate of rotation is increased with time causing a continuing increase in the angular acceleration until the carton fails. The failure force of the carton can be read directly from the force gauge or calculated indirectly from the angular acceleration, the radius of the tether from the axis to the bottom of the test carton, and the velocity of rotation at the time of failure. Therefore, at the time of failure:

$$F_f = m \cdot a_f \tag{I}$$

where
$F_f$ = Force to Failure
m = mass of carton
$a_f$ = angular acceleration at failure $$a_f = V^2/r \tag{II}$$

where,
v = peripheral velocity of the carton at failure
r = radius from the axis of rotation to the bottom of the carton, and, $$V = (RPS) \cdot C$$

where,
RPS = Revolutions per Second at time of failure
C = Circumference along the outside perimeter of the carton For practical purposes the preferred method is the use of a force gauge which can be read and recorded directly after the test is completed.

BRIEF DESCRIPTION OF THE DRAWINGS

FIGS. 3 and 4 are end views of two attachments for attaching the test carton handle to the load cell;

FIG. 5 is a plan view of a third attachment for attaching a test carton handle to the load cell; and FIG. 6 is a perspective view of part of a fourth attachment for attaching a test carton handle to a load cell.

DETAILED DESCRIPTION OF THE INVENTION

Figure 1:
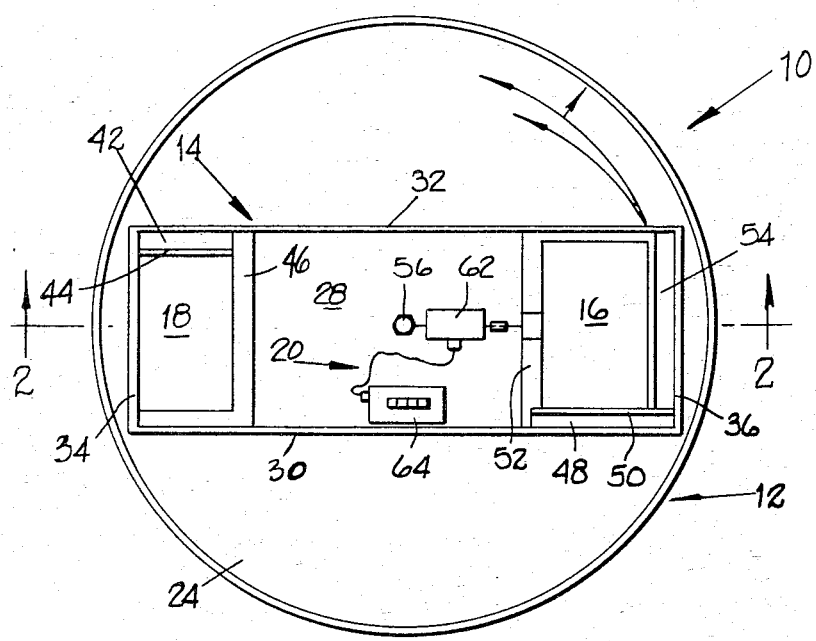
FIG. 1 is a schematic plan view of the centrifugal tester of the present invention with the partial lids not shown.
Figure 2:
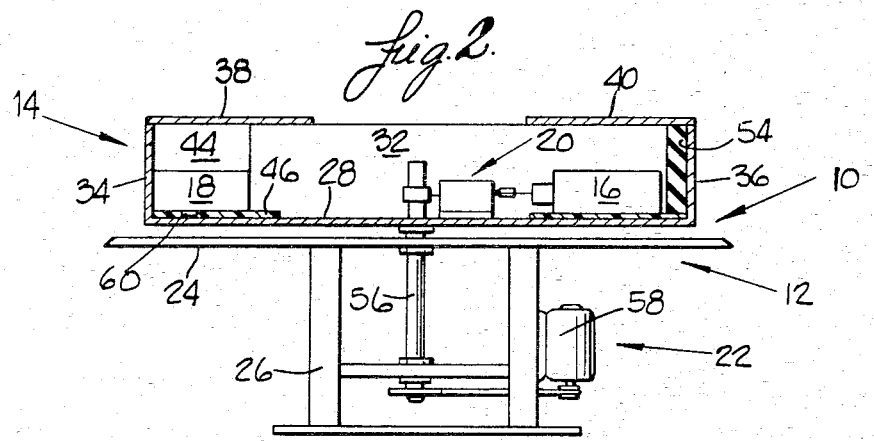
FIG. 2 is a sectional elevation view along line 2—2 of FIG. 1 with the partial lids in place.

Referring now to FIGS. 1 and 2, the centrifugal test apparatus of the present invention is generally designated by reference numeral 10. The centrifugal test apparatus comprises a support table 12, an elongated box 14 for receiving the test carton 16 and counterweight 18, a force gauge 20 for indicating the failure point of the carton 16, and a variable speed drive assembly 22 for rotating the box 14.

The support table 12 comprises a horizontal circular aluminum top 24 which is supported by steel support legs 26. The top 24 has a diameter greater than the length of the box 14 so that the box, which is rotated during testing, will not extend beyond the edge of the table top. The support legs 26 not only support the table top 24 but also provide mounts for the variable speed drive assembly 22.

The elongated box 14 is made of aluminum and has a bottom wall 28, sidewalls 30 and 32, end walls 34 and 36, and partial lids 38 and 40 which overlay the ends of the box 14. The lids 38 and 40 are each hingedly secured to the sidewall 32 along one side so that they can be raised to permit the placement of the test carton 16 and the counterweight 18 in the box for testing and the removal of the test carton 16 and counterweight 18 from the box 14 after the test has been completed. During the testing the sides of the lids opposite the hinged sides are held down in place by latches (not shown) on the sidewall 30.

A rubber pad 42 is secured to the sidewall 32 adjacent end wall 34 to cushion any impact between the counterweight and sidewall 32 and to center the counterweight in the box. The rubber pad 42 and the bottom wall 28 adjacent the end wall 34 are both provided with facing sheets 44 and 46 which are made of a material, such as TEFLON, which has a low coefficient of friction. Should the counterweight 18 not be placed up against the end wall 34 and the facing plate 44 prior to a test, these facing sheets allow the counterweight to slide into contact with both the end wall 34 and the facing sheet 44 as the box 14 begins to rotate thereby ensuring that the counterweight is properly located within the box.

A rubber pad 48 is secured to the sidewall 30 adjacent the end wall 36 to cushion any impact between the test carton 16 and the sidewall 30 and to center the test carton 16 in the box.

The rubber pad 48 and the bottom wall 28, adjacent the end wall 36 are both provided with facing sheets 50 and 52 which are made of a material such as TEFLON, which has a low coefficient of friction. When the test carton 16 is undergoing testing in the centrifugal test assembly 10, the test carton is in contact with the facing sheets 50 and 52 which allow the test carton to slide easily under the action of the centrifugal forces exerted on the test carton.

A rubber pad 54 is secured to the end wall 36 to cushion the impact when a carton fails. Without the rubber pad 54, the impact of the bottles or cans against the end wall 36 after carton failure could cause the bottles to break and the cans to rupture. While the bottom of the carton must be spaced from the rubber pad 54 during testing, it has been found that the distance between the bottom of the test carton 16 and the rubber pad 54 should be kept to a minimum to reduce the impact of the cans or bottles against the pad after carton failure. The preferred spacing is about one inch.

The box 14 is affixed at its horizontal balance point to a drive shaft 56. The drive shaft 56 is rotatably mounted in bearings in the support table 12 and is driven by a variable speed motor 58. A switch 60 can be located in the facing sheet 46 of the box 14. When the counterweight 18 is placed on the facing sheet 46, the switch 60 is closed completing the circuit so that the motor 58 can be turned on. If no counterweight is in place, the switch 60 remains open and the motor cannot be turned on. The speed of the motor is controlled by a conventional SCR control.

A conventional load cell 62 with a digital readout 64, such as a Newport Shunt Cal, Model 420, is used to measure the force of failure. One end of the load cell is secured to a collar on the drive shaft 56 by an eyebolt which allows the load cell to swing horizontally relative to the drive shaft. As shown in FIG. 3, the other end of the load cell 62 is connected through an eyebolt 66, a link 68 and a carton attachment member, to the test carton 16.

The centrifugal test apparatus 10 of the present invention is provided with several different attachments illustrated in FIGS. 3 to 6 for attaching the load cell 62 to various types of test cartons 16.

FIG. 3 illustrates an attachment 70 for attaching the load cell to the handle 72 of a basket style carrier. The attachment 70 comprises two components 74 and 76 which have rubber pads 78 and 80 that contact the sides of the carrier handle 72. The components 74 and 76 are each about two inches in width and are bolted together to clamp the attachment member to the handle. As shown, the free end of the component 74 is curved back on itself to engage the upper edge of the handle slot 82 of the basket carrier handle.

FIG. 4 illustrates an attachment 84 for attaching the load cell 62 to the handle 86 of a wrap-around or sleeve style carrier having two elongated slots 88 and 90. The attachment 84 comprises two components 92 and 94, about two inches in width, which are bolted together to clamp the attachment 84 to the handle. Component 92 is provided with a rubber pad 95 which contacts the inside of the handle 86. The attachment 84 is coupled to the link 68 in the same manner as attachment 70.

FIG. 5 illustrates an attachment 96 for attaching the load cell to the handle 98 of a wrap-around or sleeve style carrier having a pair of opposed finger holes 100 and 102. The attachment 96 comprises a T-shaped member 104 and two finger members 106 and 108. The T-shaped member 104 is coupled to the link 68 in the same manner as attachment 70. The T-shaped member 104 has two extensions 112 and 114 which each have a series of notches 116 along their inner edge. The finger members 106 and 108 are each provided with vertical slots which are hooked over the notches 116 to attach the finger members 106 and 108 to the T-shape member. The finger members are each about three-quarters of an inch wide and have extensions 118 and 120 with rubber pads 122 and 124 respectively that engage the inside of the handle 98 adjacent the finger holes 100 and 102. With the notches 116, the spacing of the finger members 106 and 108 can be adjusted to the finger hole spacing of the particular carrier being tested.

FIG. 6 illustrates a component 126 which can be substituted for one of the finger members 106 and 108 when a carrier is to be tested that has a thumb hole and an opposed slot instead of two opposed finger holes. The upper portion 128 of the component is the same as the upper portions of finger members 106 and 108 and is provided with a slot 129 for mounting the component on either of the extensions 112 and 114. However, the lower portion 130 of the component is about two and one-half inches wide. The lower portion 130 is provided with a rubber pad 132 which contacts the carrier handle adjacent the slot in the carrier.

In operation, a test carton 16 is attached to the load cell 62 by means of one of the attachments illustrated in FIGS. 3 through 6. A counterweight 18 is placed in the opposite end of the box 14. The lids 38 and 40 are then closed and latched. The motor 58 is then turned on and the box is accelerated to a rotational speed where carton failure occurs. When carton failure occurs, which can be determined audibly, the motor is turned off, the rotation of the box 14 ceases and the force required for failure is read on the digital display 64.

What is claimed is:

1. A centrifugal test apparatus for determining the failure point of a carton for packaging bottles or cans comprising:

a box for receiving a test carton and a counterweight, said box having a bottom wall, first and second sidewalls, first and second end walls, and first and second lids which overlay opposite first and second end portions of said box where the test carton and the counterweight are located during testing to prevent fragments from being thrown from said box during testing;

said box being affixed at its horizontal balance point to a drive shaft, said drive shaft being driven by a variable speed motor to regulate the rotational speed of said box and the force exerted on the test carton;

means for locating the test carton in said first end portion of said box in a spaced relationship to said first end wall and for attaching a handle of the test carton to a force gauge, said locating and attaching means simulating the gripping of the test carton by a person; and said force gauge being affixed in said box.

2. The centrifugal test apparatus of claim 1 wherein: surfaces of the box which contact the test carton have low coefficients of friction.

3. The centrifugal test apparatus of claim 1 wherein: the first end wall is provided with a layer of material on its inner surface to cushion the impact of the test carton when carton failure occurs.

4. The centrifugal test apparatus of claim 1 wherein: a control switch of the variable speed motor is located in said second end portion of the box which switch is closed by the placement of the counterweight in said second end portion.

5. A centrifugal test apparatus for determining the failure point of a carton for packaging bottles or cans comprising:

a box for receiving a test carton and a counterweight, said box having a bottom wall, first and second sidewalls, first and second end walls, first and second partial lids which overlay opposite first and second end portions of said box where the test carton and the counterweight are located during testing to prevent fragments from being thrown from said box during testing, and surfaces of the box which contact the test carton having low coefficients of friction;

said box being affixed at its horizontal balance point to a drive shaft, said drive shaft being driven by a variable speed motor to regulate the rotational speed of said box and the force exerted on the test carton;

means for locating the test carton in said first end portion of said box in a spaced relationship to said first end wall and for attaching a handle of the test carton to a force gauge, said locating and attaching means simulating the gripping of the test carton by a person;

said force gauge being affixed in said box; and a control switch for the variable speed motor located in said second end portion of the box which switch is closed by the placement of the counterweight in said second end portion.

* * * * *